United States Patent
Lodi et al.

(10) Patent No.: US 7,060,047 B2
(45) Date of Patent: Jun. 13, 2006

(54) METHOD AND DEVICE FOR SENSING THE DETACHMENT OF THE VENOUS NEEDLE FROM A PATIENT DURING AN EXTRACORPOREAL BLOOD TREATMENT IN A DIALYSIS MACHINE

(75) Inventors: Carlo Alberto Lodi, Novi di Modena (IT); Francesco Paolini, Ganaceto (IT); Enrico Canini, Mirandola (IT)

(73) Assignee: Gambro Lundia AB, Lund (SE)

(*) Notice: Subject to any disclaimer, the term of this patent is extended or adjusted under 35 U.S.C. 154(b) by 412 days.

(21) Appl. No.: 10/344,721

(22) PCT Filed: May 30, 2002

(86) PCT No.: PCT/IB02/01954

§ 371 (c)(1),
(2), (4) Date: Feb. 14, 2003

(87) PCT Pub. No.: WO02/102441

PCT Pub. Date: Dec. 27, 2002

(65) Prior Publication Data

US 2003/0176829 A1    Sep. 18, 2003

(30) Foreign Application Priority Data

Jun. 15, 2001 (IT) ............................. TO01A0582
Jun. 15, 2001 (IT) ............................. TO01A0583

(51) Int. Cl.
*A61M 37/00* (2006.01)
*C02F 1/44* (2006.01)

(52) U.S. Cl. .................. 604/6.08; 604/6.09; 210/646; 210/746

(58) Field of Classification Search ............... 604/4.01, 604/5.01, 5.04, 6.06, 6.09, 6.11, 6.16, 6.08, 604/65, 67; 210/645–646, 97, 739, 746, 210/321.71, 600, 634, 644, 195.2, 321.6, 210/321.75, 416.1, 433.1, 500.1, 500.22; 73/861.18; 422/44

See application file for complete search history.

(56) References Cited

U.S. PATENT DOCUMENTS

| | | |
|---|---|---|
| 6,663,585 B1 * | 12/2003 | Ender ........................ 604/6.08 |
| 6,932,786 B1 * | 8/2005 | Giacomelli et al. ......... 604/6.08 |
| 2003/0036719 A1 * | 2/2003 | Giacomelli et al. ........ 604/5.04 |
| 2004/0171977 A1 * | 9/2004 | Paolini et al. ............. 604/4.01 |

FOREIGN PATENT DOCUMENTS

| | | |
|---|---|---|
| FR | 2.067.572 | 8/1971 |
| WO | WO 99/12588 | 3/1999 |
| WO | WO 99/24145 | 5/1999 |
| WO | WO 01/47581 A1 | 8/2001 |

* cited by examiner

*Primary Examiner*—Patricia Bianco
*Assistant Examiner*—Leslie R. Deak
(74) *Attorney, Agent, or Firm*—Finnegan, Henderson, Farabow, Garrett & Dunner, L.L.P.

(57) ABSTRACT

A method of sensing the detachment of the venous needle (13) from a patient (P) during an extracorporeal blood treatment in a dialysis machine (1) having an extracorporeal blood circuit (2), in which an electric current is made to flow along a closed-loop path (P1) of an electrical circuit (37) formed by an electrical line (21, 22, 23) external to the extracorporeal circuit (2), a portion of extracorporeal circuit (2) directly connected to the venous needle (13), and the patient (P); a signal correlated with the electric current along the electrical line (21, 22, 23) is detected; and the signal is compared with a threshold value by means of a control unit (15).

30 Claims, 1 Drawing Sheet

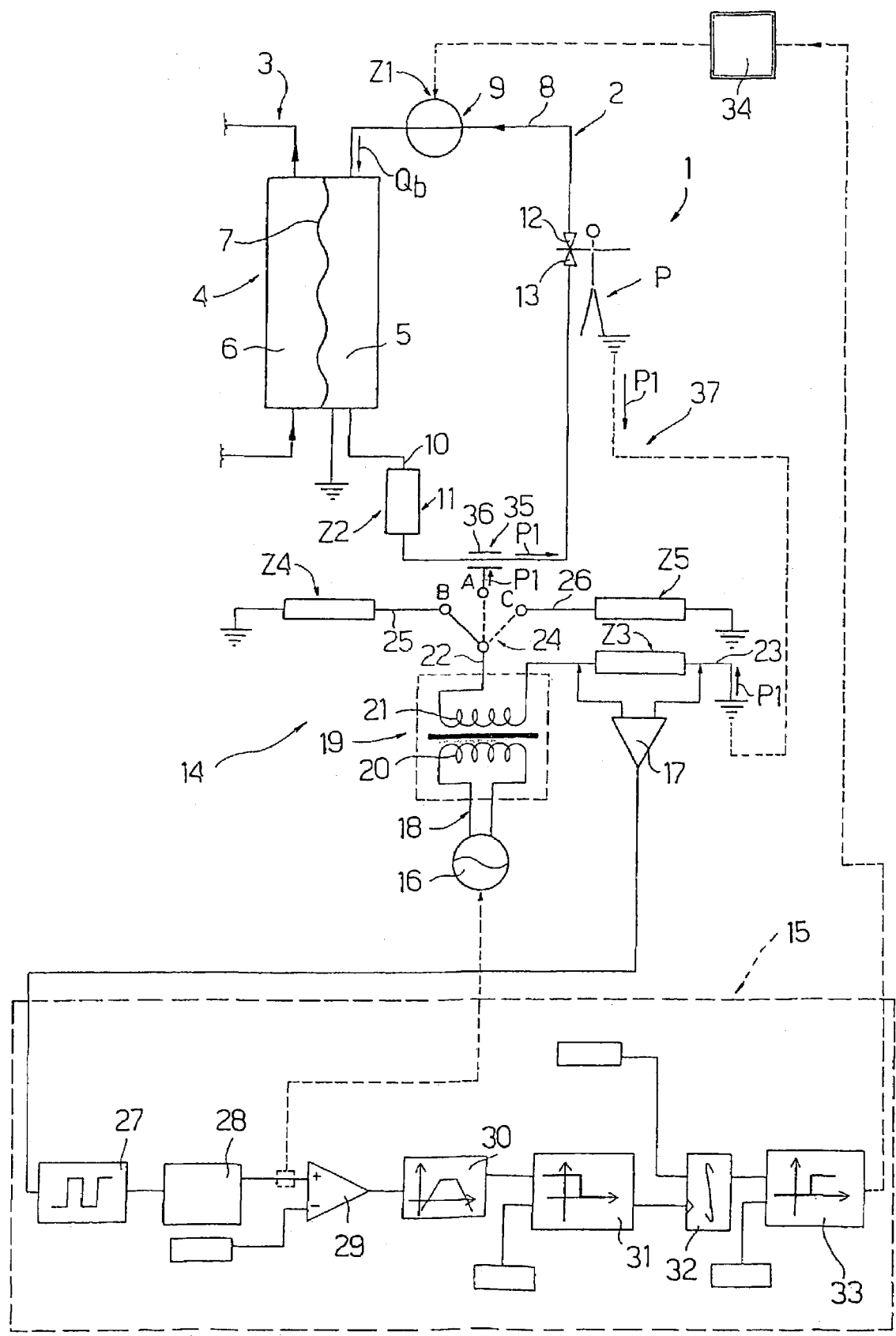

METHOD AND DEVICE FOR SENSING THE DETACHMENT OF THE VENOUS NEEDLE FROM A PATIENT DURING AN EXTRACORPOREAL BLOOD TREATMENT IN A DIALYSIS MACHINE

The present invention relates to a method of sensing the access to a patient's cardiovascular system during an extracorporeal blood treatment in a dialysis machine.

As is known, blood consists of a liquid component called the blood plasma and a corpuscular component formed by the blood cells, including the red corpuscles among other components. In renal insufficiency, the blood has, in addition to the aforesaid components, particles of low molecular weight (referred to below as solute) which have to be eliminated by a dialysis treatment carried out with a dialysis machine.

A dialysis machine of the known type generally comprises an extracorporeal blood circuit, a dialysate circuit and a filter, which is located in the aforesaid circuits and comprises a blood compartment and a dialysate compartment, which are separated from each other by a semi-permeable membrane, and through which pass, respectively, the blood to be treated and the dialysate, generally flowing in counter-current mode.

During the dialysis treatment, the undesired particles contained in the blood migrate from the blood compartment to the dialysate compartment through the semi-permeable membrane both by diffusion and by convection, as a result of the passage of some of the liquid contained in the blood towards the dialysate compartment. Thus the patient will have lost some weight by the end of the dialysis process.

The extracorporeal circuit is connected to the patient by means of an arterial needle and a venous needle, which are inserted into a fistula formed in the patient's cardiovascular system, so that they can, respectively, collect the blood to be treated and return the treated blood to the patient's cardiovascular system. The extracorporeal circuit comprises, in addition to the filter located between the venous branch and the arterial branch, a peristaltic pump and a dropper located in the arterial branch and in the venous branch respectively. The detachment of one of the aforesaid needles from the fistula causes an interruption of the access to the patient's cardiovascular system. The detachment of the venous needle, if not detected in good time, has particularly serious consequences, because it can cause a significant blood loss in the patient. Various attempts have therefore been made to provide methods for sensing the detachment of the aforesaid needles, and particularly of the venous needle.

One of the aforesaid known methods is described in WO 99/12588. This method is based on the electrical conductivity of the blood, and consists of the injection of a current into a closed circuit consisting of the extracorporeal circuit and the patient's cardiovascular system, and the measurement, by means of a measuring instrument located in the aforesaid extracorporeal circuit, of the current variations which are caused by the detachment of one or both of the needles. In this method, the current injection and the measurement of the current variation have to be carried out by inductive coupling, in other words by means of windings located at specified points along the extracorporeal blood circuit.

The method described above has various drawbacks. In particular, this method, although theoretically valid, cannot provide satisfactory results from the practical point of view, since the high electrical impedance produced by the peristaltic pump, which effectively interrupts the continuity of the blood flow, makes it necessary to operate with relatively high currents in order to make use of the low conductivity of the materials, generally PVC, which are used to form the extracorporeal circuit, the filter, the peristaltic pump and the dropper. The use of relatively high currents cannot be recommended for safety reasons in a machine connected to a patient, and, even if they could be used, it would not be possible to transmit these high currents by means of an inductive coupling, which, among other considerations, also generates parasitic currents which interfere with the measurement. In some dialysis machines, the dropper also creates a high impedance, of the same order of magnitude as that created by the peristaltic pump, and thus exacerbates one of the problems described above.

Consequently, because there is a requirement to operate with relatively low currents, and because the impedance of the peristaltic pump, and of the dropper in most cases, is high, the detachment of one of the needles causes current variations which are not easily identifiable and which can be confused with the background noise of the measuring instrument.

Furthermore, this method does not allow for the fact that the patient may be connected to earth and that the filter itself is necessarily connected to earth, since the dialysate circuit is connected to earth to meet the requirements of the safety regulations for dialysis machines. Therefore the electrical circuit assumed in the aforesaid application does not truly represent the real analogy of a dialysis machine in electrical terms.

The object of the present invention is to provide a method of sensing the detachment of the venous needle from a patient during an extracorporeal blood treatment in a dialysis machine, which overcomes the drawbacks of the prior art.

According to the present invention, a method is provided for sensing the detachment of the venous needle from a patient during an extracorporeal blood treatment in a dialysis machine comprising an extracorporeal blood circuit provided with a venous branch comprising a venous needle for accessing the patient's cardiovascular system, the said method being characterized in that it comprises the steps of:

making an electric current flow along an annular path of an electrical circuit formed by an electrical line external to the extracorporeal circuit, a portion of the venous branch, and the patient;

sensing a signal correlated with the electric current along the said electrical line; and comparing the said signal with a threshold value to detect the opening of the said electrical circuit by the use of signal processing means.

The present invention also relates to a device for sensing the detachment of the venous needle from a patient during an extracorporeal blood treatment in a dialysis machine.

According to the present invention, a device is provided for sensing the detachment of the venous needle from a patient during an extracorporeal blood treatment in a dialysis machine comprising an extracorporeal blood circuit provided with a venous branch connected to the venous needle for accessing the patient's cardiovascular system, the said device being characterized in that it comprises:

an electrical line external to the extracorporeal circuit, to form, in combination with a portion of the venous branch and the patient, an electrical circuit extending along a closed-loop path;

a sensor associated with the electrical line to detect a signal correlated with the current flowing in the said electrical circuit; and means of processing the said signal for sensing the opening of the said electrical circuit.

To enable the present invention to be more clearly understood, a preferred embodiment of it will now be described, purely by way of example and without restrictive intent, with reference to the attached FIGURE, which is a schematic view of a dialysis machine connected to a patient and fitted with a device for sensing the detachment of the venous needle for the application of the method according to the present invention.

In the attached FIGURE, the number 1 indicates the whole of a dialysis machine connected to a patient P. The machine 1 comprises an extracorporeal blood circuit 2, a dialysate circuit 3 and a filter 4, which comprises a blood compartment 5 and a dialysate compartment 6 separated by a semi-permeable membrane 7.

The extracorporeal blood circuit 2 comprises, in addition to the aforesaid compartment S of the filter 4, an arterial branch 8, in which is located a peristaltic pump 9 providing a flow $Q_b$ of blood, and a venous branch 10, in which is located a dropper 11. The branch 8 has an arterial needle 12, which, when in use, is inserted into a fistula (not shown) in the patient P to collect the blood from the cardiovascular system of the patient P, while the branch 10 has a venous needle 13, which, when in use, is inserted into the aforesaid fistula to return the treated blood to the cardiovascular system of the patient P. The branches 8 and 10 are tubes made from plastic material, generally PVC, and are used, respectively, to supply the blood to be treated to the compartment 5 and to introduce the treated blood leaving the compartment 5 into the cardiovascular system. The filter 4 and the dropper 11 are also made from plastic material, generally PVC.

The machine 1 is fitted with a device 14 for sensing the detachment of the venous needle 13. The operation of the device 14 is based on the electrical conductivity of the blood and on experimental measurements which have demonstrated that the material used to form the circuit 2, generally PVC, can be considered to be an insulator, and that both the peristaltic pump 9 and the dropper 11 can be considered to be concentrated impedances indicated by Z1 and Z2 respectively. The peristaltic pump 9 causes a cyclic interruption in the flow of blood at every half revolution of the pump 9 and thus the impedance Z1 is a function of the number of revolutions of the pump 9 and of the power supply frequency. Experimental tests have shown that the impedance Z1 is in the range from 500 to 2000 k_. The impedance Z2 is also determined by the fact that the blood flow $Q_b$ is interrupted at the dropper 11 and the value of Z2 is also in the range from 500 to 2000 k_.

The impedances of the other components of the extracorporeal circuit 2 are negligible with respect to the values of the impedances Z1 and Z2.

The device 14 comprises a control unit 15, a voltage generator 16, a voltage drop sensor 17, an electrical line 18, a transformer 19 comprising a primary 20 and a secondary 21. The voltage generator 16 sends a current along the line 18, which is connected to the primary 20 of the transformer 19, while the secondary 21 of the transformer forms a branch 22 connectable to the venous branch 10 and with a branch 23 connected to earth. The branch 23 comprises a concentrated impedance Z3 and is connected to the voltage sensor 17, which detects the voltage across the terminals of the impedance Z3. A three-way selector 24 is located in the branch 22 to interrupt the current along the branch 22 and selectively connect the secondary 21 of the transformer 19 to the venous branch 10 when the selector 24 is in the position A (shown by a broken line), to a branch 25 when the selector 24 is in the position B (shown by a solid line), and to a branch 26 when the selector 24 is in the position C (shown by a chain line). The branches 25 and 26 are connected to earth and have impedances of Z4 and Z5 respectively. The sensor 17 is connected to the unit 15, which processes the voltage signal and comprises a rectifier 27 which receives at its input the signal from the sensor 17 and supplies at its output a rectified signal, a mean value sensor 28 which has the rectified signal at its input and a mean value signal at its output, an adder 29 having the mean value signal at its input and an added signal at its output, a band-pass filter 30 having the added signal at its input and a filtered signal at its output, and a comparison unit 31 which compares the filtered signal with a threshold value and emits at its output a signal for controlling an integrator 32 connected to a comparison unit 33, which receives at its input the signal emitted by the integrator 32, compares the signal of the integrator 32 with a threshold value, and emits a control signal.

The dialysis machine 1 comprises a control unit 34, which is connected to the control unit 15 of the device 14 to receive the control signal, and to the peristaltic pump 9.

The branch 22 is formed by an electrical conductor, while the venous branch 10 is formed by a tube of plastic material, in which blood circulates when the machine is in use. The branch 22 and the venous branch 10 are electrically coupled by an electrode 35, which comprises a ring 36 placed around the venous branch 10 at a point lying between the dropper 11 and the venous needle 13. The electrode 35 may alternatively be defined by a number of rings (two or more) electrically coupled to branch 22. According to a further alternative the single electrode 35 may be defined by a plate conductive element attached to a rigid portion, such as a cassette, of the venous branch.

In electrical terms, the ring 35 forms a first plate of a capacitor, the PVC tube forms the dielectric, and the blood within the PVC tube forms the second plate. In other words, a capacitive coupling is formed between the branch 22 and the venous branch 10.

During the dialysis treatment, in other words when the blood is circulating in the extracorporeal circuit 2 between the arterial needle 12 and the venous needle 13, the device 14 is activated by connecting the patient P to earth and setting the selector 24 to the position indicated by A in the attached figure.

The voltage generated across the secondary 21 of the transformer is 100 Vpp, with a frequency of 35 kHz. An electrical current therefore flows along a closed-loop path P1 of a circuit 37 formed, in succession, by the secondary 21 of the transformer, the branch 22, a portion of the venous branch 10 lying between the electrode 34 and the venous needle 13, the patient P and the branch 23. The path P1 of the current along the circuit 37 is determined by the fact that the impedances Z1 and Z2 are much higher than the impedance Z3, and consequently the currents flowing in the only alternative paths, in which the impedances Z1 and Z2 are located, are negligible.

The applicant has found that, even if the patient P is not connected to earth, the patient P and the earth act as the opposing plates of a capacitor, and in fact the current flowing along the path P1 is not significantly affected by the connection or non-connection of the patient P to earth. This behaviour is obtained by using an alternating current at a high frequency, of more than 10 kHz in all cases.

Therefore, both in the condition in which the patient is connected to earth and in the condition in which the patient is not connected to earth, the sensor 17 detects a voltage signal across the terminals of the impedance Z3 and transmits the signal to the unit 15. The voltage signal is a sinusoidal wave which is converted to a square wave by the rectifier 27 and from which is extracted the mean value of voltage in the unit 28. A reference value is subtracted from the mean voltage in the adder 29. The resulting signal is filtered by the filter 30, which has the function of eliminating the signal variations which are slow (less than one per second) and caused by the fluctuations of the blood conductivity. In practice, the filter 30 is used to detect only the abrupt variations of voltage due to the detachment of the venous needle 13, in other words the opening of the circuit 37.

The filtered signal is compared with a threshold value in the comparison unit 31. Until the filtered signal is below a threshold value (the condition in which the venous needle 13 is connected), the comparator 31 sends a reset signal to the integrator 32, forcing the output of the integrator 32 to zero. The output signal from the integrator 32 is compared with a threshold value in the comparison unit 33, which supplies a control signal equal to zero at its output when the input signal is below the threshold value. When the filtered signal exceeds the threshold value in the comparator 31, the integrator 32 begins to integrate a constant value and sends a time-proportional output signal in such a way that the output signal from the integrator 32 exceeds the threshold value of the comparison unit 33 and the output control signal from the comparison unit 33 takes a positive value.

The output control signal from the control unit 15 is identical, for practical purposes, to the output signal from the comparison unit 33, and is transmitted to the control unit 34, which, when the control signal takes a positive value, executes a series of actions designed to prevent blood loss, such as stopping the peristaltic pump 9.

Before the start of the dialysis treatment and during the dialysis treatment, the device 14 is tested by a procedure for determining the functionality of the elements of the device 14. According to this procedure, the selector 24 is set to the position B in such a way as to form a closed circuit formed solely by the secondary of the transformer and the branches 22, 23 and 25, and current is supplied along the branch 25. The impedance Z4 is equal to the total impedance of the portion of the venous branch 10 and the patient P in the condition in which the venous needle 13 is connected. The generator 16 supplies the transformer 19 with the same voltage as that used during the dialysis treatment, and the voltage signal which is detected across the terminals of the impedance Z3 is processed by the unit 15. The selector 24 is then set to the position C in such a way as to form a closed-loop circuit formed by the secondary 21 of the transformer and the branches 22, 23 and 26. The impedance Z5 is equal to the total impedance of the portion of the venous branch 10 and the patient P in the condition in which the venous needle 13 is detached.

In fact, the test procedure simulates the operating conditions of the device 14 in such a way as to determine whether the voltage signals detected across the terminals of Z3 lie within ranges of normality and can identify the transition between the condition in which the venous needle 13 is connected and the condition in which the venous needle 13 is detached.

A further safety measure for the device 14 consists in stopping the generator 16, during the dialysis treatment, when the mean voltage signal takes values in excess of a threshold value.

In a variant which is not illustrated, the impedance Z3 and the sensor 17 are located in the branch 22 instead of the branch 23.

In a further variant which is not illustrated, the branch 23 is not earthed, but is connected directly to the patient P, who is isolated from the earth.

The invention claimed is:

1. A device for monitoring a cardiovascular access of a patient, comprising:
   an extracorporeal blood circuit having a venous branch connected to a cardiovascular access of a patient;
   an electrical line external to said extracorporeal blood circuit and having a first branch connected to said venous branch and a second branch connected to the patient either directly or through earth;
   a voltage source located between said first branch and said second branch;
   a sensor located in said first branch or in said second branch for supplying a signal corresponding to an electric current; and
   means for processing said signal to determine the state of said cardiovascular access.

2. A device according to claim 1, wherein said sensor is located in said second branch.

3. A device according to claim 1, wherein said electrical line is connected to a point of said venous branch located between a venous dropper and a venous needle.

4. A device according to claim 1, wherein said electrical line and the patient are connected to earth.

5. A device according to claim 1, wherein said voltage source comprises an alternating voltage generator to supply an alternating voltage to said electrical line.

6. A device according to claim 5, wherein said electrical line and the patient are connected to earth, and wherein said alternating voltage has a frequency such that the patient and the earth function as opposing plates of a capacitor.

7. A device according to claim 6, wherein said frequency is greater than 10 kHz.

8. A device according to claim 1, wherein said signal is a voltage signal.

9. A device according to claim 8, wherein said second branch includes an impedance and terminals associated with the impedance, the sensor being configured to measure a voltage across the terminals.

10. A device according to claim 1, wherein said means for processing said signal comprises a filter for filtering variations of said signal, said variations having a frequency less than 1 kHz per second.

11. A device according to claim 1, further comprising means for testing an efficiency of said electrical line and of said means for processing said signal.

12. A device according to claim 11, wherein said testing means comprises a selector for disconnecting said electrical line from said venous branch and for selectively connecting said electrical line to a first test impedance and to a second test impedance.

13. A device according to claim 12, wherein said first test impedance is equivalent to the total impedance of a portion of the venous branch and the patient when said venous needle is connected, said portion of the venous branch extending between a connection of said venous branch to said electrical line and a venous needle; and wherein said second test impedance is equivalent to the total impedance of said portion of the venous branch and the patient when said venous needle is disconnected, to simulate a detachment of said venous needle.

14. A device according to claim 1, further comprising a capacitive coupling configured to connect said first branch of the electrical line to said venous branch.

15. A device according to claim 14, wherein said capacitive coupling comprises an electrode provided with at least one ring placed around said venous branch, said ring and the patient's blood corresponding to the plates of a capacitor.

16. A device according to claim 14, wherein said capacitive coupling comprises a plurality of rings placed around said venous branch.

17. A device according to claim 14, wherein said venous branch includes a box comprising a transparent plastic material, and wherein said capacitive coupling further comprises an electrode, said electrode being defined by a conductive plate element in contact with said box.

18. A device according to claim 1, wherein said means for processing said signal comprises means for comparing said signal with a threshold value.

19. A method of monitoring cardiovascular access of a patient during an extracorporeal blood treatment, comprising the steps of:
providing an extracorporeal blood circuit having a venous branch connected to a cardiovascular access of a patient;
providing an electrical line external to said extracorporeal blood circuit and having a first branch connected to said venous branch and a second branch connected to the patient either directly or through earth;
providing a voltage source located between said first branch and said second branch, and a sensor located in said first branch or in said second branch for supplying a signal corresponding to an electric current;
generating an electric current along a path of an electrical circuit comprising said electrical line and said cardiovascular access;
sensing a signal corresponding to the electric current in said electrical line; and
comparing said signal with a threshold value to determine the state of said cardiovascular access.

20. A method according to claim 19, wherein said sensor is located in said second branch.

21. A method according to claim 19, wherein said electrical line is connected to a portion of said venous branch located between a venous dropper and a venous needle.

22. A method according to claim 19, wherein said second branch and the patient are connected to earth.

23. A method according to claim 19, wherein said patient and said electrical line are connected to earth, said method further including generating an alternating current having a frequency such that the patient and the earth function as opposing plates of a capacitor.

24. A method according to claim 23, wherein said frequency is greater than 10 kHz.

25. A method according to claim 19, wherein said signal is a voltage signal and said second branch includes an impedance and terminals associated with the impedance, the method further including measuring the voltage signals across the terminals associated with the impedance.

26. A method according to claim 19, further comprising filtering out variations in said signal having a frequency less than 1 kHz per second.

27. A method according to claim 19, wherein a processing means is used for carrying out said comparing step, said method further comprising testing an efficiency of said electrical line and of said signal processing means.

28. A method according to claim 27, wherein said testing step comprises disconnecting said electrical line from said venous branch and connecting said electrical line, selectively, to a first test impedance and to a second test impedance.

29. A method according to claim 28, wherein said first test impedance is equivalent to a total impedance of a portion of the venous branch and the patient when said venous needle is connected, said portion of the venous branch extending between a connection of said venous branch to said electrical line and a venous needle; and wherein said second test impedance is equivalent to the total impedance of said portion of the venous branch and the patient when said venous needle is disconnected, to simulate a detachment of said venous needle.

30. A method according to claim 19, wherein said electrical line is connected to said venous branch by a capacitive coupling.

* * * * *